Figure 1:
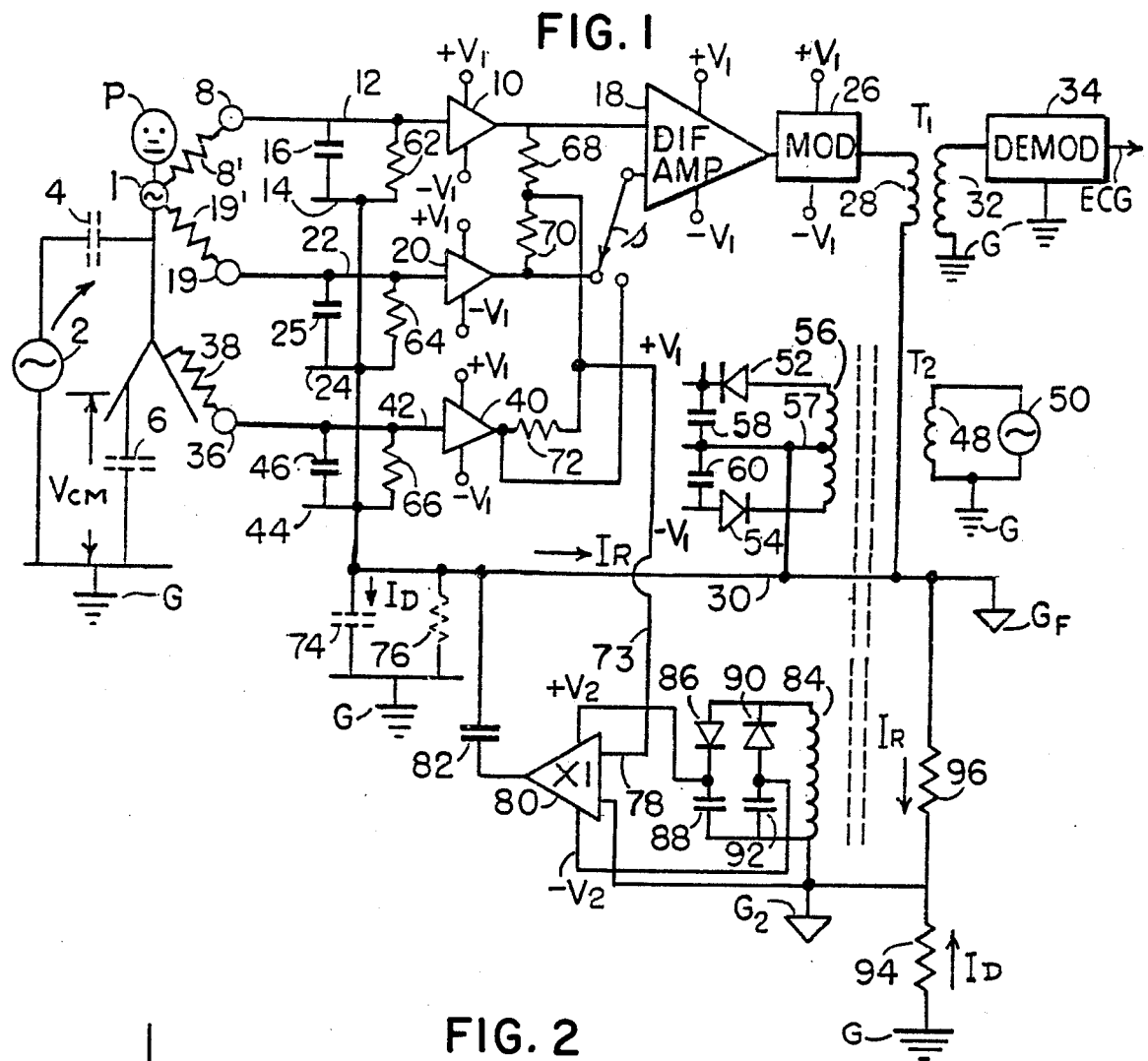

United States Patent [19]

Miller

[11] 4,191,195

[45] Mar. 4, 1980

[54] COUPLING CIRCUIT WITH DRIVEN GUARD

[75] Inventor: Arthur Miller, Brookline, Mass.

[73] Assignee: Hewlett-Packard Company, Palo Alto, Calif.

[21] Appl. No.: 940,404

[22] Filed: Sep. 7, 1978

[51] Int. Cl.² .............................................. A61B 5/04
[52] U.S. Cl. .................................... 128/696; 128/908
[58] Field of Search ................. 128/2.06 D, 2.06 E, 128/696, 709, 901, 902, 903, 639–643, 908

[56] References Cited

U.S. PATENT DOCUMENTS

| | | | |
|---|---|---|---|
| 3,690,313 | 9/1972 | Weppner et al. | 128/902 |
| 3,757,778 | 9/1973 | Graham | 128/902 |
| 3,868,948 | 3/1975 | Graetz | 128/709 |
| 3,915,154 | 10/1975 | Cosentino | 128/908 |

*Primary Examiner*—William E. Kamm

*Attorney, Agent, or Firm*—Donald N. Timbie

[57] ABSTRACT

In signal measurement circuits which are referred to a floating ground and which derive their input signals from electrodes attached to a patient's body, the effects of common mode potentials on the patient's body are minimized without requiring any patient electrodes other than those acting as signal sources by using a unity gain amplifier to drive the floating ground toward the common mode potential on the patient's body.

This process is accomplished without significantly degrading the isolation impedance between the measurement circuits and true ground.

The patient is protected from hazardous electrical shock by referencing the unity gain amplifier to a given point and connecting a large impedance between that point and true ground.

2 Claims, 2 Drawing Figures

COUPLING CIRCUIT WITH DRIVEN GUARD

BACKGROUND OF THE INVENTION

In monitoring the condition of a patient's heart, potentials produced by heart action at different points on the body are picked up by electrodes applied to these points and the differences between the potentials are coupled to the monitoring apparatus that is referenced to true ground via suitable circuits. In order to protect the patient from the possibility of electrical shock, any path between the patient and true ground must have a very high impedance. Accordingly, any circuit that is directly coupled to the patient is referenced to a floating ground called a "guard". Unfortunately, however, the patient is generally within one or more ambient electrical fields from such sources as lights or power cords that produce what is known as a "common mode voltage", $V_{CM}$, on his body. The impedance looking back from each electrode to the patient's body and the impedance looking forward from each electrode to the floating ground form a conventional four-element bridge circuit which is excited by some fraction of the $V_{CM}$. If the bridge happens to be in balance, the $V_{CM}$ introduces no problem, but this is seldom if ever the case because the impedance between each electrode and the patient's body can vary over wide limits. Any imbalance causes a portion of the common mode potential $V_{CM}$ to add to or subtract from the difference between the potentials at the points of interest on the body so as to cause errors in the signal derived therefrom.

A solution to this problem that has been used for a long time is to apply a reference electrode to the patient's body and connect it to the floating ground or guard in such manner as to make the patient have nearly the same potential as the guard, thereby reducing the effect of the common mode voltage on the floating circuit.

Whereas this scheme works well, the reference electrode is a source of error if it is not properly applied, so that as much care and time must be taken in applying it to the patient's body as in applying the other electrodes. Furthermore, because it provides no useful physiological information it may be a source of confusion to a user.

In his U.S. Patent Application filed concurrently herewith and entitled "Coupling Circuit With Driven Guard", Timothy B. Blancke has described an invention that eliminates the need for a reference electrode without in any way impairing the safety of the patient. At the same time, excellent rejection of the effects of common mode potentials is attained. The circuits connected to the patient are referred to floating ground or guard as before, but instead of driving the potential of the patient toward the common mode potential of the guard, as has been done, the guard is driven toward the common mode potential of the patient. This is accomplished by applying the common mode potential on the floating circuits to control means for causing current to flow from true ground through the stray impedance between guard and true ground. If the current has the correct value and direction, the guard will have the same common mode potential as the floating circuits. Under such conditions, the bridge is not excited by the common mode potential and no addition to or subtraction from the desired signal voltages occurs.

In order to protect the patient from electrical shock, the circuits shown in the application referred to utilize current limiters. Such devices are expensive and subject to failure.

BRIEF DESCRIPTION OF THE INVENTION

In accordance with this invention, a circuit is provided that functions in the same general manner but which protects the patient from electrical shock without using current limiters. Briefly, this is accomplished by utilizing a current supply means in the form of an amplifier that is powered by voltages referenced to a point that is D.C. coupled to floating ground by one impedance and coupled to true ground by a much larger impedance that limits the current that may flow through the patient.

THE DRAWINGS

Figure 2:
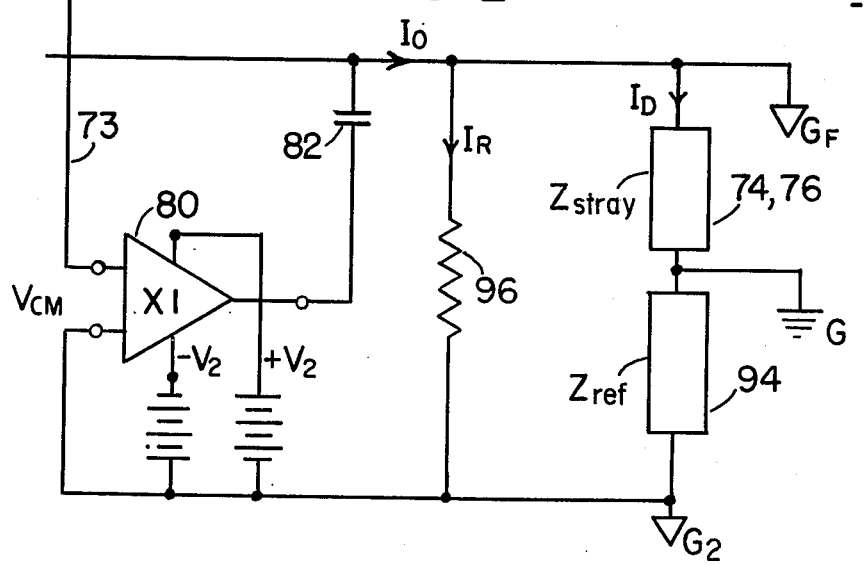

FIG. 1 is a schematic diagram of a circuit for safely coupling a patient to apparatus referred to true ground in accordance with the invention; and FIG. 2 is a portion of FIG. 1 redrawn for purposes of analysis.

The drawings illustrate the general type of circuit used for deriving a signal proportional to the voltage difference between a pair of electrodes applied to the patient's body. Stray impedances are shown in dotted lines. Source 1 supplies the desired differential physiological signals, and the numeral 2 indicates a source of undesired ambient potentials such as may be introduced by a power cord. The source 2 is shown as being coupled to a patient P via a stray capacitance represented by a capacitor 4. The common mode potential, $V_{CM}$, is at all points on the patient's body and its amplitude relative to the ambient potential depends on the voltage dividing action of the stray capacitance represented by the capacitor 4 and the stray capacitance between the patient and true ground that is represented by a capacitor 6. The impedance between a right arm electrode 8 and the patient's body is represented by a resistor 8'. The electrode 8 is connected to an input of a unity gain buffer amplifier 10 via a lead 12, and the distributed capacitance between the lead 12 and its shield 14 is represented by a capacitor 16. The output of the amplifier 10 is connected to an input of a difference amplifier 18. Similarly, a left arm electrode 19 having an impedance between it and the patient's body represented by a resistor 19' is connected to an input of a unity gain buffer amplifier 20 via a lead 22. The distributed capacitance between the lead 22 and its shield 24 is represented by a capacitor 25. The output of the amplifier 20 is connected via one terminal of a switch s to the other input of the difference amplifier 18. Although the coupling of the buffer amplifiers to the difference amplifier 18 may include a Wilson network, this is not shown in order to simplify the drawings.

The output of the difference amplifier 18 is coupled to a modulator 26 that may be one of many types. A primary winding 28 of a transformer $T_1$ is connected between the output of the modulator 26 and a guard bus 30 that is connected to a floating ground or guard indicated at $G_F$. The secondary winding 32 of the transformer $T_1$ is connected between true ground, G, and a demodulator 34 which derives the ECG signal at its output.

If other electrodes are used, as in a selectable lead or multivector system, they would be coupled to the difference amplifier 18 in a manner similar to the way in which the electrodes 8 and 19 are coupled, e.g., an electrode 36 having an impedance between it and the patient's body represented by a resistor 38 is connected to the input of an amplifier 40. The output of the amplifier 40 is connected to another terminal of the switch s. In the position shown, the switch s conducts the signal at the output of the buffer amplifier 20 to the difference amplifier 18, but with the switch s in its other position, it conducts the signal at the output of the buffer amplifier 40 to the difference amplifier 18.

The circuits directly coupled to the patient are referenced to a floating ground or guard by supplying them with operating potentials, $+V_1$ and $-V_1$, that are positive and negative with respect to the guard $G_F$. These potentials are applied to the buffer amplifiers 10, 20 and 40, the difference amplifier 18, and the modulator 26. The power supply is comprised of a transformer $T_2$ having a primary winding 48 connected at one end to true ground G and in shunt with a source of alternating current voltage 50. Oppositely poled diodes 52 and 54 are respectively connected between the ends of a secondary winding 56 of the transformer $T_2$ and its center tap 57 via capacitors 58 and 60. The guard bus 30 is connected to the center tap 57 and to the shields 14, 24 and 44. It will be understood by those skilled in the art that whereas separate transformers $T_1$ and $T_2$ are respectively used for coupling signals and providing power, techniques exist for performing both of these functions with a single transformer; but however this is accomplished, the circuits directly connected to the patient P and the primary winding 28 of the transformer $T_1$ are to be referenced to floating ground or guard $G_F$.

The Problem

The patient's body and the floating ground $G_F$, which is the point to which the inputs of the buffer amplifiers 10 and 20 are referred, are a first set of diagonally opposed points of a bridge circuit, and the electrodes 8 and 19 are a second set. One pair of arms of the bridge are formed by the impedances 8' and 19' between the patient's body and the electrodes 8 and 19, and the other pair of arms are formed by the distributed capacitances 16 and 25. The input impedances of the amplifiers 10 and 20 are so large as to have little effect on the bridge circuit even though they are part of it.

Whereas the impedances of the distributed capacitances 16 and 25 can be made very nearly equal, the impedances 8' and 19' are very seldom equal because they depend on the variable factors involved in the application of the electrodes 8 and 19 to the body. Inasmuch as the source 1 of ECG potentials is connected in series with the arms of the bridge, imbalance in the bridge per se has no effect on the form of the CG voltages delivered to the buffer amplifiers 10 and 20, but because a substantial fraction of the common mode potential $V_{CM}$ is connected between the first set of diagonal points of the bridge, namely, the patient's body and the floating ground $G_F$, any imbalance will cause unequal fractions of the common mode potential to appear at the electrodes 8 and 19 which are the second set of diagonal points of the bridge. This converts the common mode interference voltage to a differential signal applied to the buffer amplifiers 10 and 20. Because the common mode potential $V_{CM}$ is much larger than the ECG potentials, even a small imbalance in the bridge can cause a differential interference signal at the input of the difference amplifier 18 that is larger than the desired ECG voltages.

The Solution

The circuit described below drives the floating ground $G_F$ toward the potential $V_{CM}$ so that the fraction of the common mode voltage which excites the bridge circuit is greatly reduced. Therefore, regardless of the degree of imbalance in the bridge, smaller interference signals appear at the electrodes 8 and 19. If the voltage on $G_F$ is made equal to $V_{CM}$, the bridge excitation and the resulting interference becomes zero.

The following components of the circuit are common to the invention of the application referred to and the invention of this application. Bias current resistors 62, 64 and 66 are respectively connected between the inputs of the buffer amplifiers 10, 20 and 38 and the bus 30. Resistors 68, 70 and 72 of equal value are respectively connected between the outputs of the buffer amplifiers 10, 20 and 40 and a lead 73. Since the output impedance of the buffer amplifiers is low, these resistors have negligible loading effect, and they do not affect the form or magnitude of the ECG signal. A dotted capacitor 74 and a dotted resistor 76 that are shown in parallel between the bus 30 and true ground represent the distributed impedance between the guard $G_F$ and true ground.

Embodiment of This Invention

The common mode potential, $V_{CM}$, on the lead 73 is applied to a control input 78 of a unity gain amplifier 80. Its output is coupled by a capacitor 82 to the guard bus 30. The amplifier 80 is referenced to a point $G_2$ by providing operating voltages $+V_2$ and $-V_2$ that are positive and negative with respect to that point. One way of deriving such voltages is by means of a second power supply energized by a tertiary winding 84 of the transformer $T_2$. One end of the winding 84 is connected to the point of reference potential $G_2$. A diode 86 and a capacitor 88 are connected in series across the winding 84 so as to provide a voltage $+V_2$ at their junction that is positive with respect to $G_2$, and an oppositely poled diode 90 and a capacitor 92 are connected in series across the winding 84 so as to produce a voltage $-V_2$ at their junction that is negative with respect to $G_2$. A resistor 94 or other impedance, such as a capacitor whose impedance is large enough to protect the patient from harmful electric shock, serves as a means for connecting the reference $G_2$ of the amplifier 80 to true ground. A resistor is preferred because static charge can leak through it to ground. A resistor 96 is connected between the point $G_2$ and the floating ground or guard $G_F$ so as to complete the control circuit for the amplifier 80.

Operation

As previously stated, the patient and the floating ground $G_F$ are a first set of diagonal points in the bridge. The common mode potential $V_{CM}$ at the junction of the resistors 68 and 70 is applied to the input 78 of the amplifier 80. If its gain is K, its output, which is coupled by the capacitor 82 to the floating guard 30, is $KV_{CM}$. The common mode current, $I_{CM}$, flowing between the patient P and the floating ground $G_F$ or between the first set of diagonal points of the bridge, may be expressed as $$I_{CM} = \frac{V_{CM} - KV_{CM}}{z} \quad (1)$$

where z is the impedance of the circuit components between the diagonal points. The effective impedance Z between patient and true ground may be expressed as $$Z = \frac{V_{CM}}{I_{CM}} = V_{CM} \cdot \frac{z}{V_{CM}(1-K)} = \frac{z}{1-K} \quad (2)$$

Therefore, as K approaches unity, the effective impedance Z approaches infinity and the common mode current $I_{CM}$ reduces to zero. Accordingly, the differential interference voltage produced by $V_{CM}$ at the second set of diagonal points, i.e., at the electrodes 8 and 19, also reduces to zero. If K is not unity, the current $I_{CM}$ will not be zero and will be divided between the upper and lower branches of the bridge so that any imbalance will cause different fractions of $V_{CM}$ to appear at electrodes 8 and 19 and cause interference in the final display. The term "unity gain amplifier" as used herein includes an amplifier that provides unity gain or nearly unity gain.

In this circuit, the floating power supply providing the operating potentials $+V_2$ and $-V_2$ for the amplifier 80 is referenced to true ground G by the high impedance of the resistor 94 that is connected between its common point, guard $G_2$, and true ground G. This impedance provides the path from true ground G for the current $I_D$ to drive the floating guard $G_F$. $I_D$ flows back to true ground G via the stray impedance of the resistor 74 and the capacitor 76.

The stray impedance is usually largely capacitive, but, for the sake of the following calculation, assume the worst case condition, for which that stray impedance would have the same phase angle as the reference impedance 94.

Referring now to FIG. 2, if the amplifier 80 does indeed have a gain very nearly equal to unity, then the output terminal of that amplifier will be at very nearly the same potential as its input terminal. Since that input terminal is at $V_{CM}$ (by way of connection 73 to the physiological amplifier system), then $G_F$ will also be at nearly that same potential, and a current $I_D$ will flow through $Z_{Stray}$. Its value will be $$I_D = \frac{V_{CM}}{Z_{Stray}} \quad (3)$$

The same current flows in $Z_{ref}$, and if we assume equal phase angles for the two impedances, the output voltage swing of amplifier 80, which is the voltage between $G_F$ and $G_2$, will be $$\text{Output Swing} = I_D (Z_{Stray} + Z_{ref}) \quad (4)$$

$$= V_{CM} \frac{Z_{Stray} + Z_{ref}}{Z_{Stray}}$$

To keep the required amplifier output at a minimum, we would like to make $Z_{ref}$ as small as possible with respect to $Z_{Stray}$; but, to maintain high patient-to-ground isolation, we would like to make $Z_{ref}$ as large as possible. For typical constructions, and with the degree of isolation required by safety standards, the fraction $$\frac{Z_{Stray} + Z_{ref}}{Z_{Stray}}$$

will have a value near 2. Since the generally accepted maximum probable value for $V_{CM}$ is about 15 volts peak, the output terminal of amplifier 80 should be capable of swinging ±30 volts with respect to its own reference, $G_2$, while its input terminal must be capable of accepting an input swing, with respect to that same reference, of ±15 volts.

To accommodate these swings, the operating voltages for amplifier 80, $+V_2$ and $-V_2$, must exceed 30 volts and would, therefore, be of the order of 40 volts each.

The amplifier 80 must also maintain its output voltage while it is feeding the loads connected to its output circuit. Typical values for resistor 96 and $Z_{ref}$ are 1 and 22 megohms, respectively, and if we continue with our assumption of the worst-case condition where $Z_{Stray}$ is equal to, and in phase with $Z_{ref}$, then the maximum required output current will be:

$$I_0 = \frac{30}{1} + \frac{30}{22} \quad (5)$$

$$= 30.7 \text{ microamperes, peak}$$

In this discussion, we have ignored capacitor 82 because its impedance at the power line frequency was negligibly small in comparison with the amplifier load impedance. However, its presence is necessary in order to let the amplifier establish its appropriate DC operating potentials.

While the input of amplifier 80 is shown in FIG. 1 to be driven from the output terminals of all the buffer amplifiers by way of resistors 68, 70 and 72, these resistors, if they had sufficiently high values, could have been connected directly to the patient electrodes. Furthermore, if the input impedance of the differential amplifier were high enough, or the patient electrode impedances were low enough, these buffer amplifiers could be omitted altogether without changing the operation of the guard driving amplifer.

In summary, this invention provides a means for driving the floating reference point of a physiological signal amplifier to the same common mode voltage with respect to true ground as the patient who is the source of the physiological signal; and this is accomplished by an amplifier whose own reference point and power supply are isolated from ground by passive components which are not subject to the failure modes of dynamic limiters based on semiconductor devices.

What is claimed is:

1. In combination,
   a coupling circuit referred to a point of floating ground potential for transferring the difference between electrical signals supplied by electrodes on a patient's body to circuits referenced to true ground,
   a unity gain buffer amplifier having an input and an output,
   means coupling potentials on said coupling circuit to said input of said unity gain amplifier,
   means for alternating current coupling said output of said unity gain amplifier to a point of floating ground potential,
   a power supply for providing direct current operating potentials to said unity gain amplifier that are referenced to a given point,
   a first impedance connected between said given point and true ground, said impedance having sufficient value to protect a patient from electrical shock, and a second impedance connected between said given point and the point of floating ground reference of the coupling circuit.

2. Apparatus for coupling signals indicative of physiological phenomena from electrodes adapted to be applied to the body of a patient to an instrument referenced to true ground, comprising first and second buffer amplifiers, each having an input and an output, a modulator, means coupling the outputs of said buffer amplifiers to said modulator, a bus for floating ground, a first power supply for providing operating potentials referenced to said bus to said buffer amplifiers and to said modulator, a demodulator referenced to true ground, means for coupling said modulator to said demodulator, a unity gain amplifying means having an input and an output, a second power supply for providing operating potentials referenced to a given point for said amplifying means, direct current voltage coupling means connected between one of the input and output of at least one of said buffer amplifiers to said input of said unity gain amplifying means, an impedance connected between said given point and true ground, a resistor connected between said given point and said floating ground bus, and a capacitor connected between the output of said unity gain amplifier and said floating ground bus.

* * * * *

UNITED STATES PATENT AND TRADEMARK OFFICE
CERTIFICATE OF CORRECTION

PATENT NO. : 4,191,195
DATED : March 4, 1980
INVENTOR(S) : Arthur Miller

It is certified that error appears in the above-identified patent and that said Letters Patent are hereby corrected as shown below:

Column 4     line 15     "38" should read -- 40 --

Signed and Sealed this

Fifteenth Day of July 1980

[SEAL]

Attest:

SIDNEY A. DIAMOND

Attesting Officer     Commissioner of Patents and Trademarks